United States Patent [19]

Fiato et al.

[11] 4,363,765

[45] Dec. 14, 1982

[54] RHODIUM RECOVERY PROCESS

[75] Inventors: Rocco A. Fiato; Jose' L. Vidal, both of Charleston, W. Va.

[73] Assignee: Union Carbide Corporation, Danbury, Conn.

[21] Appl. No.: 250,614

[22] Filed: Apr. 3, 1981

Related U.S. Application Data

[63] Continuation of Ser. No. 70,003, Aug. 27, 1979, abandoned.

[51] Int. Cl.$^3$ .............................................. C07F 15/00
[52] U.S. Cl. ................................ 260/429 R; 549/208
[58] Field of Search ............................ 260/429 R, 338

[56] References Cited

U.S. PATENT DOCUMENTS

| | | | |
|---|---|---|---|
| 3,965,116 | 6/1976 | Cram | 260/338 |
| 3,989,799 | 11/1976 | Brown | 260/429 R |
| 4,115,433 | 9/1978 | Cosby et al. | 260/429 R X |
| 4,180,517 | 12/1979 | Vidal et al. | 260/429 R X |
| 4,199,520 | 4/1980 | Cosby et al. | 260/429 R |
| 4,257,972 | 3/1981 | Vidal et al. | 260/429 R |

OTHER PUBLICATIONS

Vidal et al., Inorganic Chemistry, vol. 17 (9), pp. 2574-2585, (1978).

*Primary Examiner*—Helen M. S. Sneed
*Attorney, Agent, or Firm*—Gary L. Wamer

[57] ABSTRACT

A particular process is provided for the recovery of rhodium values from liquid compositions. The process comprises contacting a solubilized rhodium complex with water, a crown ether and an alkaline cesium salt in the liquid phase such that a solid comprising rhodium is formed. The process is applied with particular advantage to the recovery of solubilized rhodium values derived from processes for the production of polyhydric alcohols such as ethylene glycol, and monohydric alcohols such as methanol, by the reaction of carbon monoxide and hydrogen in the presence of rhodium carbonyl complex catalysts in a homogeneous liquid medium. The invention also concerns cesium/crown ether salts of anionic rhodium complexes.

21 Claims, No Drawings

RHODIUM RECOVERY PROCESS

This application is a continuation of our prior U.S. application Ser. No. 70,003 filing date Aug. 27, 1979 now abandoned.

This invention is concerned with the recovery of rhodium values from liquid compositions.

This invention is oriented, in particular, to the recovery of rhodium values from liquid compositions associated with catalytic processes wherein the catalyst comprises rhodium in complex combination with carbon monoxide, that is, a rhodium carbonyl complex catalyst. Illustrative of such processes and catalysts are those described in U.S. Pat. No. 3,833,634, issued Sept. 3, 1974 and U.S. Pat. No. 4,133,776, issued Jan. 9, 1979. These patents describe the reaction of hydrogen and carbon monoxide in the presence of rhodium carbonyl complex catalysts at temperatures of between about 100° C. and about 375° C. and a pressure of between about 500 and about 50,000 pounds per square inch absolute (p.s.i.a.), to produce polyfunctional oxygen-containing compounds such as polyhydric alcohols and their ester derivatives. Key products are ethylene glycol and ethylene diacetate. Other products are monohydric alcohols such as methanol and ethanol, and their ether and ester derivatives. Further, U.S. Pat. No. 3,957,857, issued May 18, 1976, describes effecting the reaction in the presence of a rhodium carbonyl complex which is a rhodium carbonyl cluster exhibiting a particular infrared spectrum.

In preferred embodiments of the processes described in the aforementioned patents, the reaction is conducted as a homogeneous liquid phase so that the rhodium-containing catalyst and even the products of reaction are in solution. The solution typically requires the presence of a solvent. One function of the solvent is to keep the catalyst in solubilized form before, during and after the reaction.

Illustrative of solvents which have been found to be particularly desirable for this purpose are:

(1) tetraglyme disclosed in aforementioned U.S. Pat. Nos. 3,833,634 and 3,957,857;
(2) sulfolane as described in copending application Ser. No. 61,456, filed July 27, 1979;
(3) particular combinations of tetraglyme and sulfolane, as described in copending application Ser. No. 618,021, filed Sept. 30, 1975;
(4) gamma-butyrolactone as described in U.S. Pat. No. 3,968,136, issued July 6, 1976;
(5) cryptands as described in U.S. Pat. No. 4,11,975, issued Sept. 5, 1978; and
(6) crown ethers particularly 18-crown-6, as described in U.S. Pat. No. 4,162,261, issued July 24, 1979.

Among the beneficial effects of homogeneous reaction media containing such solvents is enhanced retention of the rhodium catalyst in solution during the reaction. Maintaining the rhodium carbonyl complex catalyst in solubilized form during high temperature operation is also particularly advantageous for obtaining high rates of product formation.

Strides have also been made in the recovery of product from the homogeneous liquid phase reaction mixture while minimizing loss of rhodium values from solution. Illustrative of such recovery methods is the extraction process described in U.S. Pat. No. 4,001,289, issued Jan. 4, 1977. In accordance with that process, the product-containing homogeneous reaction mixture is combined with water and an essentially water-immiscible organic extraction solvent for the rhodium carbonyl complex catalyst, forming a water phase containing the polyhydric alcohol and other products of the reaction and an organic solvent phase containing essentially all of the rhodium complex. The liquid phases are then separated and product is recovered from the water phase without effecting significant catalyst losses inasmuch as the water phase is essentially free of rhodium catalyst.

Further, in copending application Ser. No. 786,584, filed Apr. 11, 1977, separation of products from the reaction mixture is effected by volatilization of the products therefrom while simultaneously maintaining the mixture in contact with added carbon monoxide. In this latter process, the presence of carbon monoxide keeps the rhodium in a more soluble state in the mixture during the pressure and temperature changes from product formation to product separation.

From the foregoing it is evident that improvements directed towards enhancing the rate of product formation and facilitating product recovery, have as a common objective retention of the rhodium catalyst in solution in a solubilized form. There are, however, a variety of circumstances under which it is desirable to recover solubilized forms of rhodium from solution. For example, in protracted continuous operation, the rhodium catalyst may eventually become partially or totally spent. The catalyst may also become gradually poisoned by harmful contaminants introduced in the gaseous feed or along with the solvent and/or other components added to the system. Furthermore, in continuous operation it may be desirable to withdraw liquid purge streams. Even prior to use, catalyst stock solutions may have become contaminated or no longer useful due to inappropriate composition. To simply discard such liquid compositions containing spent, poisoned, still active or unused catalyst from the aforementioned processes, or from any other process in which a catalyst comprising rhodium is used, would, of course, be prohibitive in view of the extremely high cost of rhodium.

There is described herein a process for recovering rhodium values from liquid compositions containing solubilized forms of rhodium. The process comprises contacting a rhodium complex with water, a crown ether and an alkaline cesium salt in a liquid phase such that a rhodium-containing solid separates from the liquid phase. The solid comprises a cesium/crown ether salt of a rhodium-containing anion.

The liquid compositions from which rhodium values are recovered by the method of this invention are referred to herein as the "reaction solution" and are to be distinguished from the liquid compositions which are fed to the process of this invention as the source of the rhodium values to be recovered. The latter liquid compositions are referred to herein as the "source solution" which itself can be a reaction mixture derived from processes in which catalysts comprising rhodium are employed, prepared or reactivated. The composition of the source solution and the conditions under which it has been formed are not critical features of the rhodium recovery process described herein. In general, however, the usual source solutions are those associated with the processes described in the aforementioned patents and applications for producing polyhydric alcohols (e.g., ethylene glycol), monohydric alcohols (e.g., methanol) and other oxygen-containing products, by the reaction of hydrogen and carbon monoxide in the presence of rhodium carbonyl complex catalysts.

Although the reaction solution may contain a variety of additional components depending upon the nature of the source of the rhodium values to be recovered, the essential components are water, a crown ether, an alkaline cesium salt and a rhodium complex.

The rhodium component of the reaction solution comprises rhodium in complex combination with: carbon monoxide; or an organic-substituted ligand containing an element of Groups IV, V or VI of the Periodic Table (Handbook of Chemistry and Physics—50th Edition); or any combination thereof. Illustrative of the substituents of the organic-substituted ligands are alkyl groups of 1 to 10 carbon atoms (e.g., butyl, octyl), aryl groups (e.g., phenyl), or any combination thereof. The rhodium complex may also contain other ligands such as hydrogen, halogen, carbon, sulfur and phorphorus, in combination with carbon monoxide and/or the aforementioned organic-substituted ligands. Usually, the rhodium complex is a rhodium carbonyl complex, that is, a complex comprising rhodium which is at least in complex combination with carbon monoxide. The rhodium complexes may be added to the reaction solution as such or they may be formed in situ. For example, rhodium carbonyl complexes can be generated in situ by providing carbon monoxide to the reaction solution.

The crown ethers employed in the practice of this invention are macrocyclic organic compounds consisting essentially of carbon, hydrogen and oxygen, and have at least four oxygen hetero-atoms. They are described in U.S. Pat. No. 4,162,261 and in the numerous publications cited therein such as, in particular, the article by J. M. Lehn in "Structure and Bonding", Volume 16, pages 1-69 (Springer-Verlag, New York, N.Y. 1973), and the article by Christensen et al., *Chemical Reviews*, Volume 74, No. 3, pages 351-384 (1974). A particularly apt description of this class of organic macrocycles is that given at page 351 of the Christensen et al. article which, as adopted in modified form as a mode of describing the crown ethers used in the rhodium recovery process of this invention, is: ". . . macrocycles [which] typically contain central hydrophilic cavities ringed with . . . electronegative . . . binding atoms and exterior . . . frameworks exhibiting hydrophobic behavior. They show a pronounced ability to bind a wide variety of cations . . . and in many cases to undergo . . . conformational changes during binding".

The crown ethers employable in the practice of this invention can be monocyclic or polycyclic, and contain in the principal ring at least four oxygen atoms each separated from the other by at least two aliphatic carbon atoms in series. In the preferred embodiment of the crown ether component, the principal ring contains at least two ring oxygen atoms which are each joined to ethylene or substituted ethylene groups. The remainder of the principal ring oxygen atoms are joined to either trimethylene, tetramethylene, substituted trimethylene, or substituted tetramethylene groups, or combinations thereof. The maximum number of ring oxygen atoms in the principal ring may be as much as about 100, although the more common crown ethers contain 4 to 15 ether oxygens in the principal ring and are monocyclic. The substituted ethylene, trimethylene and tetramethylene groups contains as substituents such groups as alkyl of 1 to 8 carbon atoms, aryl groups such as phenyl and benzo, and any of the other substituents described in U.S. Pat. No. 4,162,261, the disclosure of which in this respect at column 7, lines 1 to 66, is incorporated herein by reference thereto.

A further essential component of the reaction solutions of the present invention is an alkaline cesium salt. By the expression "alkaline cesium salt" is meant any cesium compound which, when dissolved in water, provides a pH greater than 7. Accordingly, the cesium component may be any of the following including any combination thereof: inorganic compounds such as cesium hydroxide, cesium oxides, cesium carbonate, cesium bicarbonate; cesium carboxylates such as cesium formate, acetate, propionate, isobutyrate, pivalate, oxalate, maleate, succinate, lactate, glycolate, benzoate, and phthalates; and other organic salts of cesium such as cesium alkoxides (e.g., cesium methoxide, ethoxide, isopropoxide and glycoxide), cesium phenoxides, and cesium pyridinolates. From the standpoint of availability and economic considerations, the cesium compounds usually employed in the practice of this invention are the aforementioned inorganic compounds and cesium carboxylates.

It is to be understood that the alkaline cesium salt may be added to the reaction solution as such including its addition as a component of a source solution, or it may be formed in situ. For example, the cesium salt may be formed in situ by providing to the reaction solution (1) non alkaline cesium salts such as cesium halides, sulfates, phosphates and nitrates, and (2) alkaline compounds of other Group I metals such as lithium, sodium, potassium and rubidium hydroxides, oxides, carbonates, bicarbonates, carboxylates, alkoxides, phenoxides and pyridinolates. Any combination of such non alkaline cesium salts and alkaline salts of other Group I metals can be used such that the reaction solution is on the alkaline side of neutral.

The purpose of effecting the rhodium recovery process of this invention in an alkaline medium is to generate and/or sustain rhodium in the form of anionic complexes, or to enhance the degree of reduction of the anionic complexes present in the reaction solution. For example, if rhodium vaues are initially present as a complex containing $Rh^{+1}$ such as in $[Rh(CO)_2X]_2$ (where x is iodide, bromide or chloride), such complex upon contact with the aqueous alkaline reaction solution, will generate an anionic carbonyl complex(es). Further, neutral rhodium carbonyl complexes such as $Rh_4(CO)_{12}$ and $Rh_6(CO)_{16}$, will react in alkaline media to generate anionic rhodium carbonyl complexes such as $[Rh_{12}(CO)_{30}]^{2-}$ and $[Rh_6(CO)_{15}]^{2-}$. Similarly, substituted neutral rhodium complexes such as, for example, $Rh_4(CO)_x(ER_3)_{12-x}$ (x is an integer from 0 to 12) and $Rh_6(CO)_x(ER_3)_{16-x}$ (x is an integer from 0 to 16), where E is an element of Group V (e.g., phosphorus) and R is alkyl or aryl, will generate correspondingly substituted anionic rhodium complexes. Further, the degree of negative charge on anionic rhodium carbonyl clusters such as $[Rh_{12}(CO)_{30}]^{2-}$ can be further enhanced when in contact with alkaline media to generate species such as $[Rh_6(CO)_{14}]^{4-}$. In all cases, the $Cs^+$/crown ether salt of such anionic rhodium complexes are well suited for recovery from the reaction solution.

The anionic rhodium complex portion of the crown ether/cesium salts recoverable from the reaction solution can be mononuclear or polynuclear. Illustrative of the anionic mononuclear rhodium complexes are $[Rh(CO)_x(ER_3)_{4-x}]^{-1}$ where E is an element of Group V (e.g., phosphorus), the R groups are alkyl having from 1 to 10 carbon atoms (e.g., butyl), aryl (e.g., phenyl) or any combination thereof, and x is zero, 1, 2, 3 or 4. Illustrative of the anionic polynuclear rhodium complexes are:

| | |
|---|---|
| $Rh_4(CO)_{11}^{2-}$ | |
| $Rh_4(CO)_{10}H_2^{2-}$ | |
| $Rh_6(CO)_{15}^{2-}$ | |
| $Rh_6(CO)_{14}^{4-}$ | |
| $Rh_6(CO)_{15}X^-$ | (where X is iodide, chloride or bromide) |
| $Rh_7(CO)_{16}^{3-}$ | |
| $Rh_7(CO)_{16}X^{2-}$ | (where X is iodide, chloride or bromide) |
| $Rh_{12}(CO)_{30}^{2-}$ | |
| $Rh_{12}(CO)_{34}^{2-}$ | |
| $[Rh_{13}(CO)_{24}H_x]^{(5-x)-}$ | (where x is 0, 1, 2, 3 or 4) |
| $[Rh_{14}(CO)_{24}H_x]^{(4-x)-}$ | (where x is 0, 1, 2 or 3) |
| $[Rh_{15}(CO)_{27}]^{3-}$ | |

Examples of anionic rhodium carbonyl complexes which additionally contain carbon, sulfur and phosphorus ligands are: $[Rh_{12}C(CO)_{25}]^{-1}$; $[Rh_6(CO)_{15}C]^{2-}$ (described in U.S. Pat. No. 4,115,428); $[Rh_{17}S_2(CO)_{32}]^{3-}$ (described in U.S. Pat. No. 4,115,433); and $[Rh_9P(CO)_{21}]^{2-}$ (described in copending application Ser. No. 958,383, filed Nov. 7, 1978).

Conceptually, the rhodium recovery process of this invention is based on the following factors and principles:

(a) The increase in polarity which generally occurs on the addition of water to most common organic solvents miscible with water such as, for example, glymes, sulfolane, lactones and crown ethers.

(b) The ability of water to decrease the extent of the interaction of the crown ether coordination sphere of an alkali metal cation with the organic molecules in the outer spheres.

(c) The ability of crown ethers to coordinate with alkali metal cations thereby forming a complex ion with increased hydrophobicity.

(d) The competition between two organic molecules able to coordinate with alkali metal cations results in the following equilibrium:

$$S_1M^+ + S_2 \rightleftharpoons S_2M^+ + S_1$$

where:
$S_1$ is the crown ether,
$S_2$ is a non crown ether, and
$M^+$ is the alkali metal cation.

Increasing concentrations of crown ether will result in shifting the above equilibrium to the left, that is, toward the formation of the crown ether/alkali metal complex ion, with the extent of this shift depending upon the equilibrium constant of the reaction. This constant will be determined by the nature and concentration of the solvent, the nature and concentration of the alkali metal cation, the temperature, and other factors. This equilibrium is most effectively shifted towards the formation of the crown ether/alkali metal cation complex when the relative sizes of the cation and the cavity of the coordinated crown are similar. In those instances in which the cavity of the crown is slightly smaller than the radius of the cation, the presence of a large excess of crown results in the preferential formation of a 2:1 crown ether:alkali metal complex (or a "sandwich" complex) over the 1:1 crown ether:alkali metal cation complex, as follows:

$$M^+ + S_1 \rightleftharpoons MS_1^+ + S_1 \rightleftharpoons M(S_1)_2^+$$

In order to enhance the formation of the crown ether/alkali metal cation complex, alkali metal cations are employed which are less able to effectively coordinate with the non crown ether-containing components of the liquid phase than with the crown ether. From this point of view, the most effective cations in aqueous systems are those having the largest ionic radius. Finally, the use of lower temperatures enhances the degree of formation of the type of crown ether/alkali metal cation complexes involved in the precipitation of the accompanying rhodium anions as required by the electroneutrality principle.

Based on the above considerations, the essential alkali metal of choice is cesium. Given this choice, the preferred crown ether component of the reaction solutions of this invention is at least one of 12-crown-4, 15-crown-5 and 18-crown-6 and their respective alkyl- or aryl-substituted derivatives. Of these, 18-crown-6 and its alkyl- and aryl-substituted derivatives are most effective. From the standpoint of availability and cost, however, 18-crown-6 itself is usually employed in the recovery process of this invention.

In the practice of the rhodium recovery process of this invention, the molar ratio of crown ether:cesium cation in the reaction solution is at least 2:1. The most effective rhodium recovery levels are achieved with a large excess of crown ether such as crown ether:$Cs^+$ molar ratios up to 1000:1 or higher.

The ratio of the molar concentration of cesium cation to rhodium in the reaction solution, that is, $[Cs^+]:[Rh]$, ranges between about 0.1 and about 5.0, and is more usually between about 0.1 and about 1.0.

A further relationship is that between the crown ether and water. In general, the weight ratio of crown ether:water in the reaction solution is between about 50:1 and about 1:50, and is usually from about 10:1 to about 1:10.

The concentration of crown ether in the reaction solution is at least 5 weight percent and can be as high as about 90 weight percent, based on the total weight of the reaction solution. The minimum lower concentration of crown ether is usually at least about 25 weight percent.

The rhodium content of the reaction solution will depend, of course, on the rhodium content of the source solution which is to be treated by the process of this invention. Generally, the reaction solutions from which rhodium is most effectively recovered are those containing from about 500 to about 30,000, usually from about 1000 to about 12,000, parts per million (ppm.) of rhodium.

The order and manner by which the essential components of the reaction solution are brought together is not a critical feature of this invention. In addition, reasonable rhodium recovery efficiencies can be achieved by the process of this invention when the reaction solution contains the essential components within the above-stated ranges. However, when it is desired to achieve a maximal rhodium recovery efficiency, the essential components are employed in specific ratios necessary to achieve that efficiency from a given source solution. Such optimum ratios of these components can be determined experimentally by self-directed optimization techniques.

The rhodium recovery process of this invention is effected in the liquid phase. Usually, the process is effected at ambient temperature (e.g., 18°–30° C.), and at pressures from about atmospheric up to about 100 psia. It is to be understood, however, that temperatures up to the boiling point of the reaction solution may be used. Likewise, the physical constraint on the lower temperature is dictated by the freezing point of the reaction solution. Although the rhodium recovery process is usually effected at pressures no higher than about 100 psia., it is to be understood that the process may be effected at higher pressures such as up to about 500 psia.

The rhodium source, crown ether, alkaline cesium salt and water are combined, usually with agitation by any suitable means such as mechanical or magnetic stirring. Agitation is preferably continued at least until the resulting reaction solution is homogeneous. The generation of rhodium-containing solids in the reaction solution is allowed to occur until such time that the formation of additional amounts of solids ceases. The usual residence time is from about 1 to about 72 hours. The solids are recovered by any liquid-solids separation technique such as, for example, decantation, centrifugation or filtration.

Depending upon the projected end use of the recovered rhodium values comprising anionic rhodium complexes, the recovery process of this invention can be effected in the presence of an inert gas such as nitrogen or argon, or a gas that will generate rhodium carbonyl complexes or enrich the carbonyl content thereof such as carbon monoxide and carbon monoxide/hydrogen mixtures, or in some specific cases, the process may be effected in the presence of air.

In general, the usual source solutions which are treated by the process of this invention to recover rhodium values therefrom, are those associated with processes for producing polyhydric alcohols (e.g., ethylene glycol), monohydric alcohols (e.g., methanol) and other oxygen-containing products, by the reaction of hydrogen and carbon monoxide in the presence of rhodium carbonyl complex catalysts at temperatures from about 100° C. to about 375° C. and pressures from about 500 to about 50,000 psia., as described, for example, in aforementioned U.S. Pat. Nos. 3,833,634, 3,957,857 and 4,133,776. The homogeneous liquid phase in which such processes are typically effected usually comprises one or more of the following components:

(a) Inorganic and organic Lewis base promoters such as, in particular, the organic nitrogen Lewis bases exemplified by morpholine, N-methylmorpholine and pyridine, and any of the other Lewis bases disclosed, for example, in U.S. Pat. No. 4,162,261 beginning with column 11, line 16 through column 13, line 37 and at column 16, lines 31–44, which disclosure is incorporated herein by reference thereto. Other suitable amine promoters are the dimorpholines (e.g., ethylenedimorpholine) described in copending application Ser. No. 56,967, filed July 12, 1979.

(b) Salt promoters including ammonium salts, and salts of metals of Group I and Group II of the Periodic Table, and others disclosed in the aforementioned U.S. patents. Illustrative of typical salt promoters are halides, hydroxides, alkoxides, phenoxides, pyridinolates and carboxylates such as sodium fluoride, potassium acetate, cesium fluoride, cesium pyridinolate, cesium formate, cesium acetate, cesium benzoate, cesium p-methylsulfonyl benzoate, rubidium acetate, magnesium acetate, strontium acetate, ammonium formate, ammonium benzoate and the like. Of further interest is U.S. Pat. No. 3,952,039 which describes the use of alkali metal salt promoters in amounts from about 0.5–1.5 atoms of cation per six atoms of rhodium, to achieve the optimum rate of formation of alkane polyol product.

(c) Solvents such as those described in the aforementioned U.S. patents and copending U.S. applications such as tetraglyme, sulfolane, tetraglyme/sulfolane mixtures, gamma-butyrolactone, cryptands and crown ethers, particularly 18-crown-6. Other useful solvents are 2,2-di(alkyl)-substituted gamma-butyrolactones wherein the alkyl group has from 1 to 12 carbon atoms, as described in copending application Ser. No. 890,969, filed Mar. 28, 1978.

(d) Phosphine oxides such as triphenyl-, tripropyl- and tributylphosphine oxides, as described in copending application Ser. No. 920,828, filed June 30, 1978; the description in said application of suitable phosphine oxides is incorporated herein by reference thereto.

The source solutions associated with the above-described processes for producing polyhydric and monohydric alcohols from carbon monoxide and hydrogen in liquid homogeneous reaction media and which may be fed to the rhodium recovery process described herein, may be any process stream containing rhodium values. Such streams include precursor catalyst stock solutions and premixes thereof with solvent and/or promoters, reaction mixtures containing the polyhydric and monohydric alcohol products, reaction mixtures from which product has been recovered, recycle and purge streams, and the like. It is to be understood that the various components which may be present in such source solutions (e.g., amines, glymes, sulfolane, lactones, potassium salts, phosphine oxides, as well as the oxygen-containing products) do not interfere with the successful operation of the rhodium recovery process of this invention. It is also noted that when such source solutions, or any other source solutions, already contains a crown ether and/or alkaline cesium salt, they will, of course, supply not only the rhodium values to the reaction solution of the rhodium recovery process of this invention, but they will serve as at least a partial source of the essential crown ether and/or alkaline cesium salt components as well. For example, when the crown ether and cesium salt are both present in the source solution in amounts which provide the reaction solution of the present invention with the requisite proportions described hereinabove, the source solution need only be combined with an appropriate amount of water to effect generation of the $Cs^+$/crown ether salt of the rhodium-containing anion. To the extent required, the salt may be subjected to reactivation procedures or otherwise recycled to the glycol-producing process.

Other source solutions which can be treated by the method of this invention to recover rhodium values therefrom are those associated with the rhodium-catalyzed carbonylation of methanol to acetic acid, as described in U.S. Pat. No. 3,769,329. Other suitable source solutions are those associated with hydroformylation processes for producing aldehydes from an olefin, carbon monoxide and hydrogen using rhodium catalysts containing carbon monoxide and phosphine ligands, as described, for example, in U.S. Pat. No. 3,527,809.

The following examples are merely illustrative and are not presented as a definition of the limits of the invention.

In the following Examples, the "Rhodium Recovery Efficiency" was determined as follows:

$$100 - \left[\left[\frac{Rh_2 \times \frac{W_2}{W_1}}{Rh_1}\right] \times 100\right]$$

where:
$Rh_1$ is the original rhodium content in parts per million (ppm) of the source solution;
$Rh_2$ is the rhodium content remaining in solution after separation of the rhodium-containing solids;
$W_1$ is the weight of the source solution to be treated; and
$W_2$ is the weight of the reaction solution.

It is to be understood, however, that for any particular source solution having a given rhodium content, the maximum efficiency in rhodium recovery that can be achieved will be determined by the rhodium saturation level of the reaction mixture (i.e., the reaction solution after the formation of the solids has ceased). For example, given two source solutions which vary only in their rhodium content (e.g., 100 and 12000 ppm.) and which therefore, after treatment under the same conditions will provide final solutions of the same rhodium saturation level (e.g., 50 ppm.), a lower rhodium recovery efficiency (e.g., 50 versus 99.58%) will be achieved with the source solution having the lower rhodium concentration.

Since the rhodium saturation level of a given final solution will vary with its composition, a different final rhodium concentration will be obtained upon varying the nature and/or ratios of the components of the liquid phase. For example, the weight of unrecoverable rhodium in the final solution will be increased upon increasing the volume of this solution. Similarly, the rhodium saturation level of the reaction solution will vary appreciably upon use of source solutions comprised of different organic solvents such as crown ethers, glymes, or sulfolane.

EXAMPLE 1

The purpose of this example is to illustrate application of the method of this invention to the recovery of rhodium values from a product-containing reaction mixture comprising a solubilized rhodium carbonyl complex(es), cesium cations, 18-crown-6 and oxygen-containing products, as the source solution.

(A) Preparation of Source Solution

The reaction mixture was produced in a 150 ml. capacity stainless steel reactor capable of withstanding pressures up to 7,000 atmospheres. The reactor was charged with a premix of: 3.0 millimoles (mmoles) of rhodium dicarbonylacetylacetonate ["Rh(CO)$_2$AcAc"]; 1.25 mmoles of pyridine; 0.65 mmole of cesium benzoate; and 75 ml. of 18-crown-6. The reactor was sealed and further charged with a gaseous mixture containing equal molar amounts of carbon monoxide and hydrogen to a pressure of 12,500 psi. Heat was applied to the reactor and its contents; when the temperature of the mixture inside the reactor reached 190° C., as measured by a suitably placed thermocouple, an additional adjustment of carbon monooxide and hydrogen (H$_2$:CO=1:1 mole ratio) was made to bring the pressure back to 12,500 psi. The reaction was effected while maintaining the pressure at this level and the temperature at 260° C. for 0.70 hour. After the reaction was terminated, the reactor and its contents were cooled to room temperature, the excess gas vented and the reaction product removed. In addition to solubilized rhodium and initially charged cesium salt, pyridine promoter and 18-crown-6 solvent, the reaction mixture (i.e., the source solution) contained the following products as determined by gas chromatographic analysis using a Hewlett Packard FM TM model 810 Research Chromatograph (weight percent): ethylene glycol (10.02), methanol (3.56), glycol monoformate (0.19), methyl formate (0.46), and residual tetraglyme (7.78) used to rinse out the reactor.

(B) Recovery of Rhodium Values

Upon analysis by atomic absorption, the source solution produced in accordance with part (A) of this example was found to contain 2252 ppm. rhodium. A 10 gram portion thereof was combined with 10 grams of water. The reaction solution was stirred at room temperature under one atmosphere of carbon monoxide for three hours. The solids which formed were separated by centrifuging. The supernatant solution was faint yellow in color and, upon atomic absorption analysis, was found to contain 54.4 ppm. of rhodium. Taking into account the fact that the source solution (10 grams) had been diluted by an equivalent weight of water (10 grams), the percentage of rhodium remaining in the reaction solution, based on the rhodium content of the source solution treated, is [(54.2×2)/2252×100], or 4.81 percent, corresponding to a Rhodium Recovery Efficiency of 95.2 percent. Atomic absorption analysis of another sample of the supernatant solution showed the presence of 52.3 ppm rhodium, corresponding to a Rhodium Recovery Efficiency of 95.35 percent, giving an average value of 94.28±0.07 percent.

For the purpose of comparison, a 10 gram portion of the source solution containing 2252 ppm. rhodium described under part (A) of Example 1, was combined with 10 grams of a 44 weight percent aqueous solution of formic acid. The reaction solution was stirred at room temperature under one atmosphere of carbon monoxide for three hours. After centrifuging it was observed that a small amount of solids had formed and that the supernatant liquid still had a burgundy color. The rhodium content (atomic absorption analysis) of the supernatant liquid was 503.6 ppm., corresponding to a Rhodium Recovery Efficiency of 55.3 percent.

EXAMPLE 2

The purpose of this example is to further illustrate the application of the method of this invention to the recovery of rhodium values from reaction mixtures containing rhodium carbonyl complex catalysts which have been exposed to the high pressure reaction or carbon monoxide and hydrogen.

(A) Preparation of Source Solution

A reaction mixture was prepared following the procedure described under part (A) of Example. The reactor was charged with a premix of: 3.0 mmoles of Rh(CO)$_2$AcAc; 0.65 mmole of cesium benzoate; 1.25 mmoles of pyridine and 75 ml. of 18-crown-6. The gaseous feed contained equal molar amounts of CO and H$_2$. The reaction was carried out at a temperature of 260° C. and a pressure of 12,500 psi. for a period of 0.81 hours. In addition to the initially charged cesium salt and pyridine promoters and 18-crown-6 solvent, the reaction mixture contained (weight percent): ethylene glycol (9.39); methanol (3.69); methyl formate (0.423); and residual tetraglyme (5.54) used to wash the reactor.

(B) Recovery of Rhodium Values

Upon atomic absorption analysis, the source solution produced in accordance with part (A) of this example was found to contain 2573.0 ppm. rhodium. An 18.25 gram portion thereof was combined with 28.00 grams of water. The solution was stirred at room temperature under carbon monoxide (1 atmosphere) for a period of approximately 24 hours. The resultant mixture was then centrifuged and the supernatant liquid isolated. Analysis of the supernatant liquid showed that it contained 41.3 ppm of rhodium, corresponding to a Rhodium Recovery Efficiency of 95.93 percent.

EXAMPLE 3

The purpose of this example is to demonstrate the beneficial effect of cesium cation in the recovery of rhodium values from source solutions which initially contain 18-crown-6 and potassium cation.

(A) Preparation of Source Solutions

Three potassium salt-containing source solutions, designated I, II and III, were prepared following the procedure described under part (A) of Example 1. The details of each preparation are given below.

Source Solution I. The $CO/H_2$ gaseous feed was fed to a solution containing: 1.5 mmoles of rhodium dicarbonylacetylacetonate, 0.5 mmole of potassium benzoate, 7.0 mmoles of N-methylmorpholine and 75 ml. of 18-crown-6. The reaction was effected at a temperature of 280° C. and a pressure of 15,000 psi. for a period of 0.73 hours. In addition to the solubilized rhodium carbonyl catalyst species, the initially charged potassium salt and N-methylmorpholine promoters, and the 18-crown-6 solvent, the reaction product mixture contained (weight percent): methanol (4.451), ethanol (0.232), ethylene glycol (8.957), propylene glycol (0.304), methyl formate (0.624), glycol monoformate (0.275), and residual tetraglyme wash (3.335). Analysis (atomic absorption) of Source Solution I showed it to contain 834.7 ppm. rhodium.

Source Solution II. In the preparation of this solution, the $CO/H_2$ feed was fed to a premix containing: 1.5 mmoles of rhodium dicarbonylacetylacetonate, 0.375 mmole of potassium acetate, 4.0 mmoles of N-methylmorpholine and 75 ml. of 18-crown-6. The reaction was carried out at a temperature of 270° C. and a pressure of 15,000 psi. for a period of 0.80 hours. In addition to the solubilized rhodium carbonyl catalyst species, the initially charged potassium salt and pyridine promoters and 18-crown-6 solvent, the source solution contained (weight percent): methanol (4.765), ethanol (0.216), ethylene glycol (9.003), methyl formate (0.595), glycol monoformate (0.520), and residual "wash" tetraglyme (3.868). Atomic absorption analysis of Source Solution II showed it to contain 994.8 ppm. rhodium.

Source Solution III. In the preparation of this solution, the $CO/H_2$ gaseous feed was fed to a solution containing: 1.5 mmoles of rhodium dicarbonylacetylacetonate, 0.375 mmole of potassium benzoate, 100 mmoles of water and 75 ml. of 18-crown-6 solvent. The reaction was carried out at 260° C. and a pressure of 15,000 psi for a reaction period of 0.466 hour. In addition to the solubilized rhodium carbonyl catalyst, the initially charged potassium salt and N-metylmorpholine promoters, and 18-crown-6, the source solution contained (weight percent): methanol (2.751), ethylene glycol (4.488), methyl formate (0.140), water (1.917) and residual "wash" tetraglyme (1.736). Analysis of Source Solution III showed it to contain 1556.5 ppm. rhodium.

(B) Recovery of Rhodium Values Without Addition of $Cs^+$

To each of 10 gram samples of Source Solutions I, II and III there was added 10 grams of distilled water. The respective reaction mixtures were then stirred at room temperature for approximately 24 hours. Source Solutions I and II gave turbid solutions which appeared to contain a precipitate after about 6 hours of stirring. Source Solution III appeared to stay homogeneous; however, after about 6 hours of stirring, frothing was observed but decreased after 18 hours of stirring. At the end of the 24-hour period, the respective solutions were centrifuged and the supernatant liquids, designated Solutions I-1, II-1 and III-1, respectively, were analyzed by atomic absorption to determine their rhodium content. The results of these analyses and the Rhodium Recovery Efficiencies are given in the following Table I.

TABLE I

| Source Solution Treated | Rhodium Analyses, ppm. | | Rhodium Recovery Efficiencies, % |
|---|---|---|---|
| | Initial[1] | Final[2] | |
| I | 834.7 | 243.4 | 42 |
| II | 994.8 | 322.0 | 32 |
| III | 1556.5 | 732.0 | 6 |

[1]Rhodium content of source solution.
[2]Rhodium content of supernatant liquid.

(C) Recovery of Rhodium Values With Addition of $Cs^+$

A 10 gram portion of Source Solution I which contained 18-crown-6 and potassium cation but no cesium salt, was combined with 200 milligrams of cesium acetate and 10 grams of water. The resultant reaction solution was stirred at room temperature. After several minutes of mixing it appeared that precipitate was forming. The stirring was continued for a period of 3.0 hours and was then centrifuged. The supernatant liquid had a faint yellow color and was analyzed to determine its rhodium content. The analysis showed that the supernatant liquid contained 102.1 ppm of rhodium. Inasmuch as Source Solution I before dilution contained 834.7 ppm. of rhodium, the Rhodium Recovery Efficiency was 75.5%. Inspection of Table I shows that when Source Solution I was simply treated with an equivalent weight of water without adding cesium salt, the Rhodium Recovery Efficiency was only 42%.

EXAMPLE 4

This example is set-forth to further illustrate that the combination of crown ether and water without the presence of $Cs^+$ is not adequate for the efficient recovery of rhodium values from product-containing reaction mixtures produced by the reaction of CO and $H_2$ under relatively high pressure in the presence of rhodium carbonyl complex catalysts.

(A) Preparation of Source Solution

This solution was prepared following the procedure described under part (A) of Example 1. The reactor was charged with a premix of 1.5 mmoles of rhodium dicarbonylacetylacetonate; 0.375 mmole of potassium benzoate; 4.5 mmoles of N-methylmorpholine; 200 mmoles of water; and 75 ml. of 18-crown-6. The gaseous feed contained equal molar amounts of CO and $H_2$. The reaction was carried out at a temperature of 270° C. and a pressure of 15,000 psi for a period of 0.866 hours. In addition to the rhodium values, the initially charged potassium salt and amine promoters and the 18-crown-6 solvent, the source solution contained (weight percent): methanol (2.560), ethylene glycol (8.675), water (0.789) and residual tetraglyme wash (3.486).

(B) Recovery of Rhodium Using 18-crown-6

A portion of the source solution described under part (A) of this example was filtered. A 6.0 gram portion of the filtered source solution (rhodium content 1401.1 ppm) was weighed out into a 25 ml. round bottom flask equipped with a magnetic stirrer and a carbon monoxide purge. Also added to the reaction mixture were 3.0 grams of 18-crown-6 and 3.0 grams of distilled water. The mixture was magnetically stirred approximately 72 hours under one atmosphere of carbon monoxide. At the end of this period of time the mixture was filtered and the solids were separated. Rhodium analysis of the filtrate showed that it contained 727.3 ppm. rhodium. Inasmuch as the source solution contained 1401.1 ppm. rhodium prior to dilution, it is evident that the filtrate contained the original rhodium content, and thus the Rhodium Recovery Efficiency was nil.

(C) Recovery of Rhodium Using 15-crown-5

A 6.0 gram portion of the filtered source solution produced as described under part (A) of this example, was treated in the same manner as described under part (B) of this example except that, instead of adding 3.0 grams of 18-crown-6 thereto, 3.0 grams of 15-crown-5 was added. The rhodium content of the filtrate was 619.8 ppm. rhodium (atomic absorption analysis). Thus, 88.47 percent of the original rhodium content (1401.1 ppm) of the solution remained in solution, corresponding to a Rhodium Recovery Efficiency of 11.53 percent.

The results of this example demonstrate that, although the use of 15-crown-5 in place of 18-crown-6 did lead to some rhodium recovery from the K+-containing reaction product, the 11.53 percent recovery is far less than the recoveries achieved when cesium salts are present.

EXAMPLE 5

This example illustrates application of the method of this invention to the recovery of solubilized rhodium carbonyl complexes from source solutions which have not been subjected to the high pressure reaction of carbon monoxide and hydrogen to ethylene glycol and other oxygenated compounds. The particular solutions treated are designated Solution A and Solution B, respectively.

(A) Preparation of Source Solutions A and B

The particular materials used in the preparation of these solutions are as given in Table II.

TABLE II

| Source Solution: | A | B |
| --- | --- | --- |
| Ingredients Added | | |
| Rh(CO)$_2$AcAc, grams | 0.76 | 0.76 |
| Potassium benzoate, grams | 0.130 | — |
| Cesium benzoate, grams | — | 0.177 |
| N-methylmorpholine, grams | 0.590 | — |
| 4-Hexadecylmorpholine, grams | — | 1.83 |
| 18-crown-6, grams | 43.0 | 43.0 |

In the preparation of these source solutions, the 18-crown-6 was melted in a CO-purged tube under carbon monoxide (15 psi) at about 50° C. The amine and benzoate salt were next added. After stirring the mixture for about 30 minutes, the rhodium dicarbonylacetylacetonate was added. The respective mixtures were then stirred at 50° C. under one atmosphere of carbon monoxide for approximately 24 hours. Small amounts of solids which formed were separated by filtration.

(B) Recovery of Rhodium From Source Solutions A and B

To each of two 10 gram portions of Solution A, and to a 10 gram portion of Solution B, an equivalent weight of water (10 grams) was added. These three rhodium recovery experiments are referred to for convenience as A-1, A-2 and B-1, respectively. In addition, 200 milligrams of cesium acetate was added to A-2. Each of the three mixtures was stirred at room temperature under carbon monoxide (one atmosphere) for 12 hours. The solids which formed were separated by centrifuging, and the respective filtrates (or "final solution"), were analyzed for rhodium content. The rhodium contents and cations present are given in Table III which also includes the rhodium contents of Solution A and Solution B prior to dilution with water, as well as the Rhodium Recovery Efficiencies.

TABLE III

| Rhodium Recovery | A-1 | A-2 | B-1 |
| --- | --- | --- | --- |
| Solution A, grams | 10 | 10 | — |
| Water added, grams | 10 | 10 | — |
| Solution B, grams | — | — | 10 |
| Water added, grams | — | — | 10 |
| Cation | K+ | K+/Cs+ | Cs+ |
| Rhodium Content, ppm. | | | |
| Source Solution | 5420 | 5420 | 2631 |
| Final Solution | 266 | 221 | 27.8 |
| Rhodium Recovery Efficiency % | 90.2 | 92 | 97.9 |

The results of Table III indicate that, notwithstanding the fact that each of Solutions A and B contained 18-crown-6 and alkali metal cations, the rhodium recovery achieved in B-1 upon addition of water to Source Solution B (which contained Cs+) was 97.9 percent, whereas the rhodium recovery achieved in A-1 upon addition of water to Solution A (in which the sole cation was K+) was 90.2 percent. The results also show that the addition of cesium cation to Solution A in A-2 assisted in removing an additional 1.8 percent rhodium value from the solution. Also of interest is the observation that, whereas the Rhodium Recovery Efficiencies achieved in the experiments described under part (B) of Example 3 (wherein no Cs+ was added to K+-containing Source Solutions I, II and III) were only 42, 32 and 6 percent, the percent rhodium recovered from K+-containing Solution A in A-1 (wherein there also was no addition of Cs+) was substantial (90.2 percent). There are a number of possible explanations for the low rhodium recovery usually obtained from cesium-free, potassium-containing solutions which have been subjected to the relatively high pressure reaction of carbon monoxide and hydrogen. One explanation is that there may be a change in the identity of the rhodium carbonyl catalytic species during the course of the high pressure CO/H$_2$ reaction such that the potassium salt thereof is converted to a more soluble form. Another explanation is that the presence of the usual products of the reaction such as ethylene glycol and methanol, render the potassium salt of rhodium carbonyl clusters more soluble in the reaction mixture and thus more difficult to recover.

EXAMPLE 6

The purpose of this example is to demonstrate that the method of this invention can be applied to remove rhodium species of different solubilities from solution, especially sulfur-poisoned rhodium carbonyl catalysts.

(A) Source Solution Treated

In this example, the CO/hydrogen feed was charged to a reaction mixture containing (parts by weight): rhodium dicarbonylacetylacetonate (0.827), cesium benzoate (0.225), ethylenedimorpholine (0.761), sulfolane (30.7), tetraglyme (24.3) and ethylene glycol (1.1). This particular run was carried out continuously at a temperature of 250° C. and a pressure between 8000 and 15,000 psi over a period of about 10 days.

(B) Recovery of Rhodium

To a 20 gram portion of the source solution produced in accordance with part (A) of this example, there was added 10 grams of 18-crown-6. After stirring for 5 minutes at 40° C., 10 grams of water were added. The mixture was stirred for 22 hours, after which the solid which had formed was separated by filtration and dried. A sample of the solid was washed with ether and dried under a carbon monoxide atmosphere and subjected to infrared analysis. The infrared spectral pattern of the solid showed three significant infrared bands at about 2010 $cm^{-1}$, about 1845 $cm^{-1}$ and about 1810 $cm^{-1}$, each plus or minus 10 cm $^{-1}$. This pattern is characteristic of the decaheptarhodium disulfido triacontadicarbonyl trianion having the empirical formula, $[Rh_{17}(S)_2(CO)_{32}]^{3-}$. The infrared spectral pattern of the sulfido anion was not detected on analysis of the filtrate. This indicates that the concentration of this species had been substantially reduced. The filtrate was subjected to two analyses by atomic absorption to determine its rhodium content. The results are given in the following Table IV which also includes the rhodium analysis on the source solution prior to the time it was treated in accordance with part (B) of this example, as well as the Rhodium Recovery Efficiency.

TABLE IV

| Rhodium Analysis, ppm. | (1) | (2) | Average |
|---|---|---|---|
| Source Solution | 5756 | 6306 | 6031 |
| Final Solution | 1752 | 1805 | 1778.5 |
| Rhodium Recovery Efficiency, % | 39.12 | 42.75 | 41 |

(C) Recovery Of Rhodium

Another sample (400 grams) of the source solution prepared in accordance with part (A) of this example was combined with 200 grams of deionized water and 200 grams of 18-crown-6 while being stirred and maintained under 1 atmosphere pressure of carbon monoxide. After 24 hours, the treated solution was filtered. The recovered solid was vacuum-dried before being subjected to elemental analysis. Results of the elemental analysis of the product, which is the cesium/18-crown-6 salt of the aforementioned decaheptarhodium disulfido triacontadicarbonyl trianion, that is, $[Cs(C_{12}H_{24}O_6)_2]_3[Rh_{17}(S)_2(CO)_{32}]$, are given in Table V where the calculated values are for $C_{104}H_{144}O_{68}Cs_3S_2Rh_{17}$.

TABLE V

| | % Calculated | Percent Found (1) | (2) |
|---|---|---|---|
| C | 26.59 | 30.99 | 30.92 |
| H | 3.07 | 4.00 | 4.01 |
| N | — | Nil | 0.02 |
| Cs | 8.50 | 7.96 | 8.12 |
| S | 1.36 | 0.88 | 1.00 |
| Rh | 37.30 | 37.82 | 37.26 |

The filtrate was combined with 100 ml. of deionized water and stirred for 24 hours under one atmosphere of carbon monoxide. The precipitate which formed was isolated by filtration and analyzed. The results of the analyses are given in Table VI.

TABLE VI

| | Percent Found (1) | (2) | (3) |
|---|---|---|---|
| C | 12.99 | 13.10 | 9.08 |
| H | 2.48 | 2.31 | 2.38 |
| N | 0.18 | Nil | — |
| Cs | 2.33 | — | — |
| S | Nil | <0.02 | — |
| Rh | 38.69 | 39.00 | 40.11 |

The low sulfur content of this additional rhodium-containing precipitate generated from the initial filtrate may be indicative of the essentially selective removal from the source solution of sulfur-poisoned rhodium from uncontaminated rhodium species.

EXAMPLE 7

This example illustrates application of the method of this invention to the preparation and recovery of crown ether/$Cs^+$ salts of anionic rhodium carbonyl clusters.

A solution of $Rh(CO)_2AcAc$ (12.0 grams, 47.0 mmoles), and $CsPhCO_2.3 H_2O$ (2.8 grams, 9.52 mmoles) in tetraglyme (950 ml) was charged to a high pressure autoclave after $H_2S$ (8.2 mmoles) had been added to the solution. The system was pressurized to 6000 psi. with carbon monoxide and hydrogen ($CO:H_2 = 1:1$) and allowed to react for about 72 hours at 150° C. After venting the solution to ambient conditions, it was added to a mixture of 18-crown-6 (1000 ml., 1133 grams) and water (38000 ml., 38000 grams). The formation of a violet solid occurred immediately. The system was allowed to stand overnight; the precipitate was removed by filtration. This product has an infrared spectrum (in organic polar solvents, e.g., acetone, tetrahydrofuran) corresponding to that of $[Rh_{17}(S)_2(CO)_{32}]^{3-}$, and a Rh/Cs atom ratio, determined by atomic absorption, of 5.66 corresponding to that of the crown ether/$Cs^+$ salt of the anion. The filtrate was analyzed by atomic absorption for rhodium. The rhodium concentration of the filtrate (5.0 ppm) was corrected for the "rhodium concentration" read in the atomic absorption spectrometer for distilled water (4.0 ppm), to give an actual rhodium concentration for the filtrate of 1.0 ppm. The Rhodium Recovery Efficiency is 99.16 percent.

What is claimed is:

1. The process for the recovery of rhodium values which comprises contacting a rhodium complex with a crown ether, an alkaline cesium salt and water in a liquid phase such that a rhodium-containing solid is formed.

2. The process of claim 1 in which the rhodium complex comprises rhodium in complex combination with carbon monoxide, or an organic-substituted ligand comprising at least one element of Groups IV, V and VI, or any combination thereof.

3. The process of claim 1 in which the rhodium complex contains as an additional ligand at least one of hydrogen, halogen, sulfur, phosphorus and carbon.

4. The process of claim 1 in which carbon monoxide is provided to said liquid phase.

5. The process of claim 1 in which the cesium salt is inorganic.

6. The process of claim 1 in which the cesium salt is a cesium carboxylate.

7. The process of claim 1 in which the liquid phase additionally contains a potassium salt.

8. The process of claim 1 in which the crown ether is 18-crown-6.

9. The process of claim 1 in which the crown ether is 15-crown-5.

10. The process of claim 1 in which the crown ether is 12-crown-4.

11. The process of claim 1 in which the rhodium values are derived from a process wherein polyhydric and monohydric alcohols are produced by the reaction of carbon monoxide and hydrogen in the presence of a rhodium carbonyl complex catalyst.

12. The process of claim 1 in which the rhodium values are derived from a hydroformylation process for producing aldehydes by the reaction of an olefin, carbon monoxide and hydrogen in the presence of a rhodium catalyst containing a phosphine ligand.

13. The process for the recovery of rhodium values which comprises introducing a liquid composition containing a solubilized rhodium carbonyl complex to an aqueous liquid phase reaction mixture and contacting said rhodium carbonyl complex in said aqueous liquid phase with an alkaline cesium salt and a crown ether such that a solid comprising a salt of an anionic rhodium carbonyl complex is formed.

14. The process of claim 13 in which said liquid composition containing the solubilized rhodium carbonyl complex is derived from a process for the production of polyhydric alcohols by the reaction of carbon monoxide and hydrogen in the presence of a rhodium carbonyl complex in a homogeneous liquid phase at a temperature between about 100° C. and about 375° C. and a pressure between about 500 and about 50,000 pounds per square inch absolute.

15. The process of claim 13 in which the crown ether is 18-crown-6.

16. The process of claim 13 in which the cesium salt is a cesium carboxylate.

17. The process of claim 13 in which said anionic rhodium carbonyl complex is in association with a cesium/crown ether complex cation.

18. Cesium/crown ether salts of anionic rhodium carbonyl complexes.

19. Cesium/18-crown-6 salts of anionic rhodium carbonyl complexes.

20. The cesium/18-crown-6 salt of an anionic rhodium sulfido carbonyl cluster.

21. The salt of claim 20 in which the anionic rhodium sulfido carbonyl cluster has the empirical formula, $[Rh_{17}(S)_2(CO)_{32}]^{3-}$.

* * * * *